United States Patent [19]
Wilson

[11] Patent Number: 5,240,187
[45] Date of Patent: Aug. 31, 1993

[54] MEDICAL WASTE TREATMENT DEVICE AND METHOD

[75] Inventor: Joseph H. Wilson, Speedway, Ind.

[73] Assignee: Ecomed, Inc., Indianapolis, Ind.

[21] Appl. No.: 704,455

[22] Filed: May 23, 1991

[51] Int. Cl.$^5$ .......................................... B02C 19/12
[52] U.S. Cl. ........................................ 241/21; 241/99;
241/199.12; 241/282.1; 241/606; 99/510;
366/314
[58] Field of Search ............... 241/99, 199.12, 282.1,
241/282.2, 21, 92, 285; 99/510; 366/314

[56] References Cited

U.S. PATENT DOCUMENTS

| | | | |
|---|---|---|---|
| 1,592,601 | 7/1926 | Hines | 241/282.2 |
| 1,744,597 | 1/1930 | Vasconcellos | 241/277 X |
| 2,635,784 | 4/1953 | Benny et al. | 220/373 |
| 2,660,210 | 11/1953 | Berglind . | |
| 2,820,595 | 1/1958 | Schumacher | 244/100 X |
| 2,857,729 | 10/1958 | Zoldok | 241/277 X |
| 3,156,278 | 11/1964 | Otto | 241/282.2 |
| 3,389,864 | 6/1968 | Topinka . | |
| 3,434,518 | 3/1969 | Motis | 241/199.12 |
| 3,493,022 | 2/1970 | Mantelet | 241/199.12 |
| 3,528,469 | 9/1970 | Mantelet . | |
| 3,596,692 | 8/1971 | Swanke | 241/199.12 |
| 3,814,332 | 6/1974 | Nakao | 241/99 X |
| 3,901,349 | 8/1975 | DeNoyer | 241/100 X |
| 4,194,697 | 3/1980 | Lembeck | 241/92 |
| 4,269,364 | 5/1981 | Moriconi et al. . | |
| 4,275,848 | 6/1981 | Webb, Sr. | 241/285 R X |
| 4,578,185 | 3/1986 | Wilson et al. | 210/85 |
| 4,586,666 | 5/1986 | Fox | 241/199.12 X |
| 4,609,156 | 9/1986 | Boele | 241/199.12 |
| 4,618,103 | 10/1986 | Wilson et al. | 241/41 |
| 4,619,409 | 10/1986 | Harper et al. . | |
| 4,637,561 | 1/1987 | Edberg | 241/188.1 |
| 4,809,915 | 3/1989 | Koffsky et al. . | |
| 4,813,624 | 3/1989 | Williams | 241/282.2 |
| 4,816,307 | 3/1989 | Honeycutt | 206/366 X |
| 4,852,814 | 8/1989 | Amiote et al. | 244/282.2 X |
| 4,860,961 | 8/1989 | Hilgarth | 241/92 |
| 4,878,627 | 11/1989 | Otto | 241/199.12 |
| 4,884,756 | 12/1989 | Pearson . | |
| 4,889,290 | 12/1989 | Koffsky et al. . | |
| 4,955,548 | 9/1990 | Rahill | 241/199.12 X |
| 4,971,261 | 11/1990 | Solomons . | |
| 4,984,747 | 1/1991 | Lechner | 241/92 X |
| 4,984,748 | 1/1991 | Kimura | 241/606 X |
| 5,018,675 | 5/1991 | Gateaud | 241/282.2 |
| 5,054,696 | 10/1991 | Mennel et al. | 241/606 X |

FOREIGN PATENT DOCUMENTS

| | | | |
|---|---|---|---|
| 1394972 | 3/1965 | France | 241/282.1 |
| 1025432 | 2/1986 | Japan | 241/282.1 |
| 725700 | 4/1980 | U.S.S.R. | 241/282.1 |
| 1142167 | 2/1985 | U.S.S.R. | 241/282.1 |
| 1546076 | 2/1990 | U.S.S.R. | 241/282.1 |

*Primary Examiner*—Mark Rosenbaum
*Assistant Examiner*—Frances Chin
*Attorney, Agent, or Firm*—Willian Brinks Olds Hofer Gilson & Lione

[57] ABSTRACT

A cart-mounted or counter-top-mounted cabinet encloses a processing flask assembly located in an upwardly opening tub portion of the cabinet and which supports a drive motor below the cabinet. A blade-mounting impeller in the flask assembly is received on a motor output coupling when the flask assembly is installed in the tub. The motor, when operated, drives the blades in rotation to move and cut waste materials inserted through the open top of the flask. After a batch of waste has been processed, the flask assembly is removed from the tub and the minced and disinfected contents are dumped into suitable waste receivers with absorber material.

25 Claims, 4 Drawing Sheets

MEDICAL WASTE TREATMENT DEVICE AND METHOD

BACKGROUND OF THE INVENTION

1. Field of the Invention

This invention relates generally to machines for disintegrating trash materials, and more particularly to equipment for mincing and decontaminating infectious waste items.

2. Description of the Prior Art

A great variety of equipment ha been devised for disposing of trash of various kinds and sizes. Examples could range from a hammer as a simple example, to an automobile shredder as a more complex example. Of greater interest to the treatment of medical waste is the machine disclosed in U.S. Pat. No. 4,619,409 issued Oct. 28, 1986 to which I contributed. It is a comparatively large stationary machine for disintegration and decontamination of hospital waste materials in relatively large volumes. But there are many facilities which do not have such volumes of waste materials, space for such a large machine, or funds to buy such large and expensive machines. A couple of examples are medical and dental offices. One effort to deal with the waste materials of such facilities is represented in U.S. Pat. No. 4,971,261 issued Nov. 20, 1990 to Solomons. That patent discloses a device that is intended to be a portable desk-top device. It has a cylindrical body 11, cover 12, one-way feed opening 13 in the cover 12, a motor driven rotating blade 20 in the body to fragment the waste, a sweeper blade agitation member 21 rotated by the blade drive motor, and a cut-out 12C of the cover 12 which can be rotated to a position of registry with a discharge opening 14 in the cylindrical body 11 and which communicates with the disposal chute 15 for discharge of the fragmented particles into the jar 23 which contains sterilizing solution. Then the jar, with sanitized and fragmented items is said to be disposed of as ordinary trash. Solomons apparently was not intended to deal with soft waste items. Also, the decontamination treatment is not done until after the fragmenting.

The waste from a physician's or dentist's office and for which safe disposal is needed, includes not just hard items such as needles, syringes and vials, but also soft items such as bandage material and rubber gloves. It is desirable to avoid the necessity of sorting these things before disposal. The prior art equipment known to me in a size suitable for portable, desk-top or counter-top use in a comparatively small facility, cannot suitably handle such a variety of materials.

SUMMARY OF THE INVENTION

Described briefly, according to a typical embodiment of the present invention, a machine suitable for portable or counter-top location employs a processing flask assembly mounted in an upwardly opening receiver which supports a drive motor below the flask assembly, all of which is isolation-mounted to a counter-top or a movable cabinet. The flask assembly includes a blade-mounting impeller receivable on a motor output coupling when the flask assembly is installed in the receptacle. The motor, when operated, drives the blades in rotation to move and cut waste materials inserted through the top of the flask. The machine is operated in a batch processing manner and, after a load of waste materials has been minced and decontaminated, the flask assembly is removed and the minced and decontaminated contents are drained and dumped into suitable waste receivers.

DESCRIPTION OF THE PREFERRED EMBODIMENT

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 1:
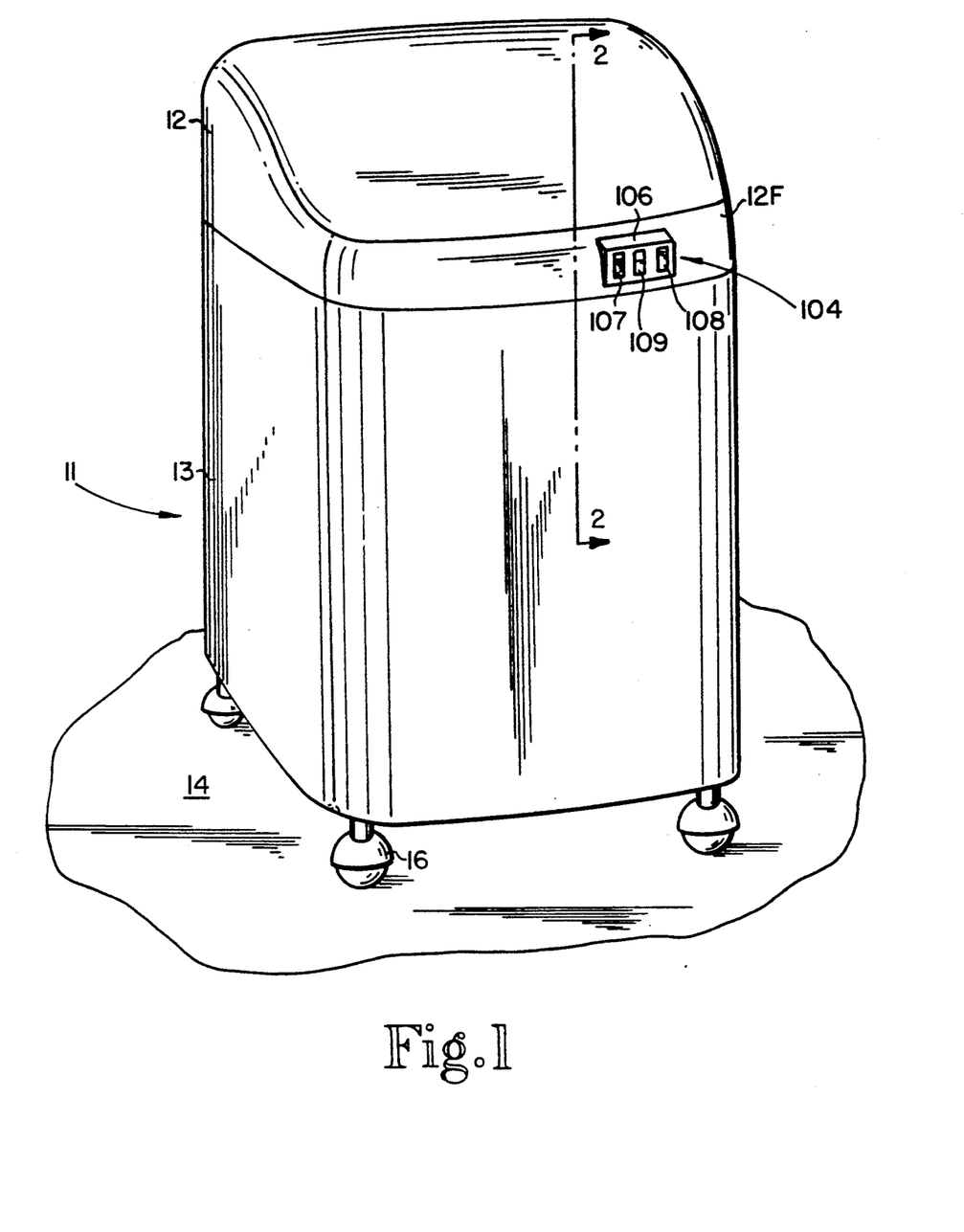
FIG. 1 is a pictorial view of a portable waste treatment device according to my invention.
Figure 2:
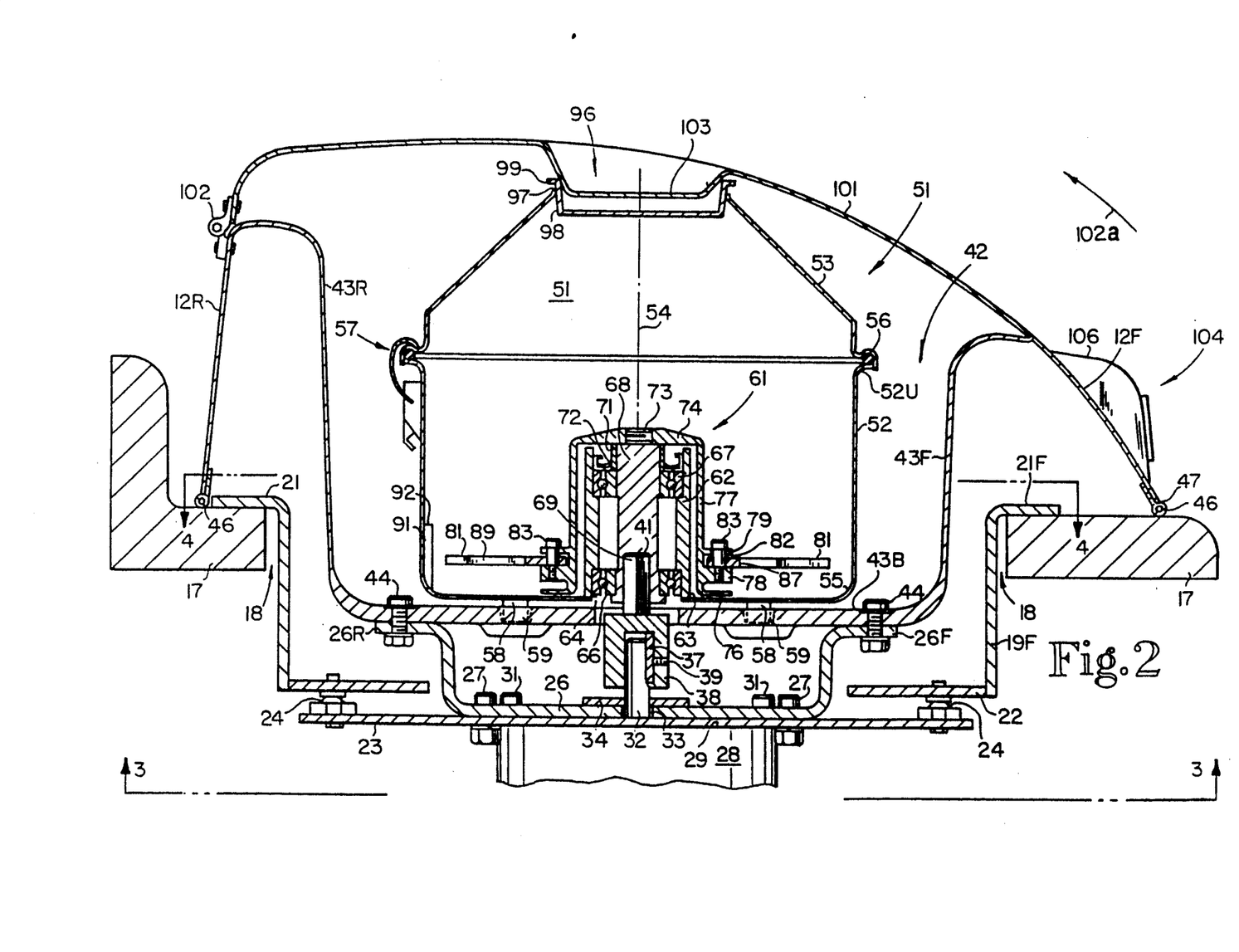
FIG. 2 is an enlarged fragmentary vertical section through a portion of the cabinet taken at line 2—2 in FIG. 1 and viewed in the direction of the arrows and showing some interior details.
Figure 3:
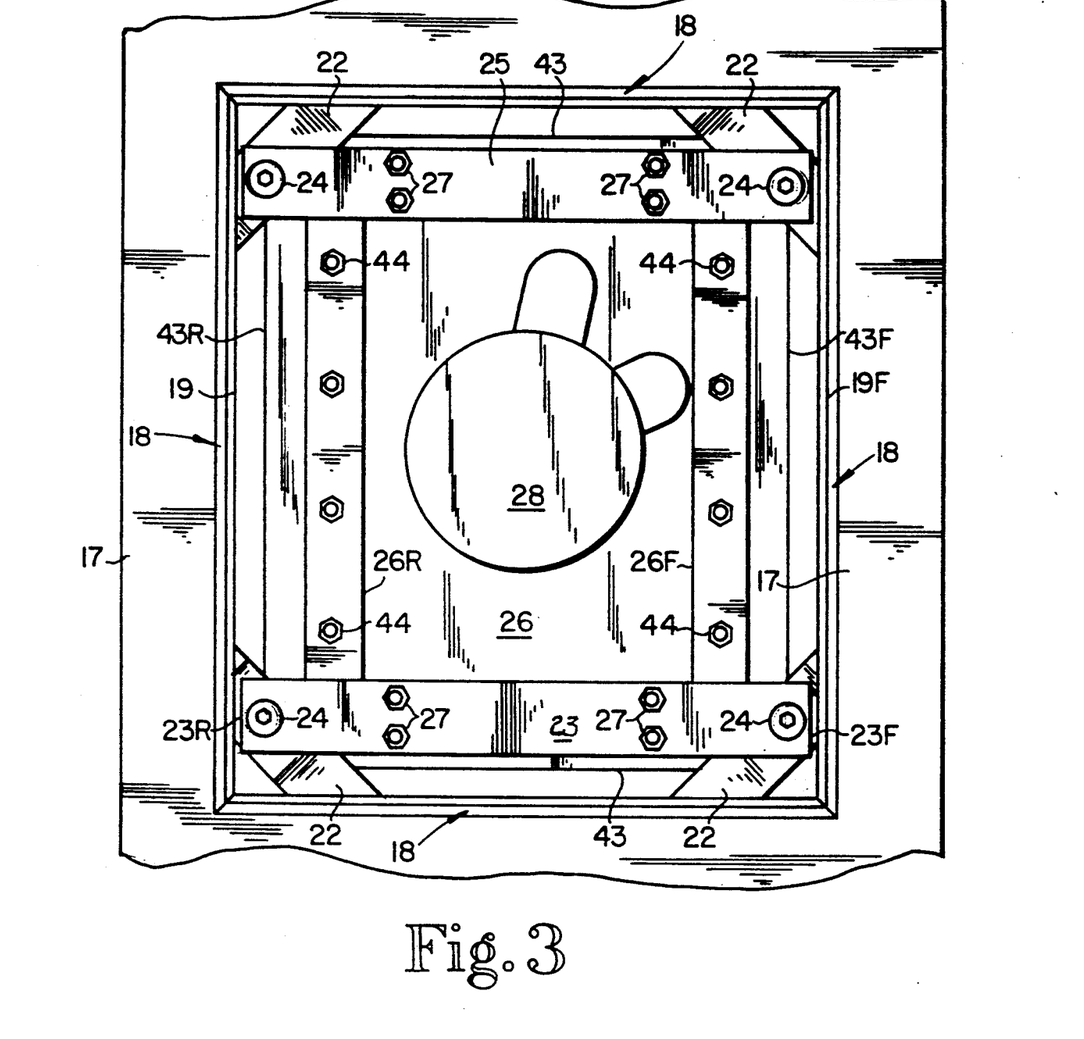
FIG. 3 is a fragmentary section taken at line 3—3 in FIG. 2 and viewed in the direction of the arrows.

Referring now to the drawings in detail, and particularly FIG. 1, a floor-mounted, mobile unit 11 includes a main cabinet 12 mounted on the top of a cart 13 which is movable along the floor 14, being supported on four casters 16, one at each corner. Referring now to FIG. 3, and regardless of whether a mobile cart 13 or a stationary counter top is the site for the present invention, it will include a support 17 which, in the illustrated embodiment, is rectangular in shape, framing a central opening 18 in which the waste treatment device is mounted according to the present invention. For this purpose, a rectangular frame 19, typically metal, is provided with an outwardly extending perimetrical flange 21 (FIGS. 2 and 4) and is mounted on the support 17 and may be secured to it in any suitable manner. The portions of frame 19 and flange 21 that are at the front of the machine are designated 19F and 21F. Frame 19 has a gusset 22 welded to it at each of the four corners of the frame. An isolation strap 23 having a front end 23F and rear end 23R is mounted to the frame gussets 22 at the respective ends by means of isolator couplings 24. An identical strap 25 and mounting arrangement is provided at the opposite side of the frame 19.

A motor mount plate 26 is mounted on top of the two straps, with four fasteners 27 securing each side of the plate to each of the two straps 23 and 25. In the illustrated example, the fasteners are socket head cap screws with nuts. This motor mount plate is generally U-shaped as shown best in FIG. 2. The motor 28, having a standard C-face 29, is fastened to the bottom center of the plate 26 by four socket head cap screws 31. The motor shaft 32 extends up through a central aperture 33 in plate 26 and is provided with a slinger ring 34 immediately above the plate 26. The motor shaft has a standard square keyway to receive a standard square key 37 in coupling 38 to which the key is secured by set screw 39. The upper end of the coupling 38 is provided with a ¼ inch square cross section at 41.

The outwardly turned front and rear flanges 26F and 26R, respectively, of the motor mount plate support the main cabinet 12. The cabinet has a front wall 12F, and a rear wall 12R and is molded in one piece of fiberglass reinforced plastic with a generally centralized tub portion 42 which is generally rectangular in configuration as shown by the front and rear walls 43F and 43R, respectively, and the side walls 43 in FIG. 4. The floor 43B of the tub is secured to the outwardly extending flanges 26F and 26R of the motor mounting plate by four fasteners 44 through each of the flanges, these fasteners typically being socket head cap screw and nut assemblies.

A hollow bulb gasket 46 is secured to the inside of the cabinet outer shell around the entire perimeter of the lower edge 47 of the shell. This gasket 46 lightly but sealingly engages the top surface of the support 17 entirely around the perimeter of the cabinet. However, it does not provide support for the cabinet since that is supported by the motor mount plate supporting the bottom 43B of the cabinet tub portion.

The flask assembly 51 of the present invention includes a flask lower housing 52 and flask top housing 53, both of which are symmetrical about the central axis 54. The flask lower housing has an outwardly turned upper circular flange 52U supporting an O-ring 56 which supports the circular bead at the bottom of the flask top housing. The top and lower housings are fastened together by over-center lever operated spring clamps 57 such as are available from Dzus Fasteners of West Islip, N.Y. 11795. The bottom of the flask lower housing has four circularly spaced feet 58 which are received in sockets 59 in the floor 43B of the cabinet tub portion. These feet support the flask assembly in the cabinet tub. They also prevent the flask assembly from rotating in the tub.

Figure 4:
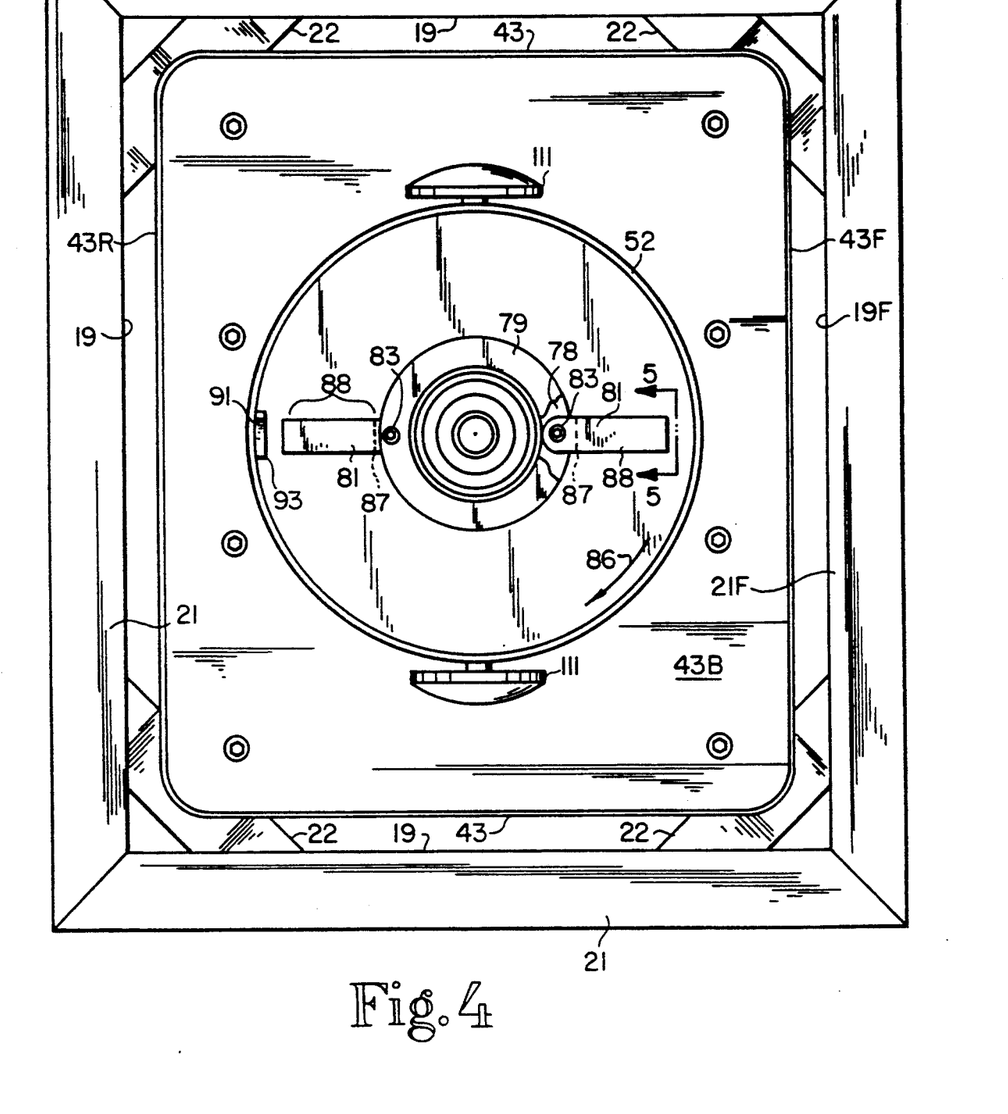
FIG. 4 is a section taken at line 4—4 in FIG. 2 and viewed in the direction of the arrows.
Figures 5, 6:
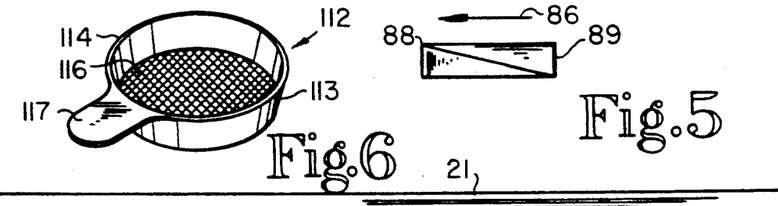
FIG. 5 is an end view of a blade taken at line 5—5 in FIG. 4 and viewed in the direction of the arrows.
FIG. 6 is a perspective view of a strainer plug used in the practice of my invention.

An impeller assembly 61 is mounted in the flask assembly. It is located and supported by a bearing mount cylinder 62 which is welded to the bottom of the flask lower housing at 63 around the central opening 64 in the flask bottom. This bearing mount cylinder receives the lower ball bearing assembly 66 and the upper ball bearing assembly 67. The inner race of each of these ball bearing assemblies fittingly receives outer cylindrical surfaces of the impeller shaft 68 which has an octagonal internal spline or socket at 69 received on the square upper end of the coupler 38. The upper portion of the impeller shaft has a sleeve 71 pressed thereon above the inner race of the upper bearing 67. This serves to engage a lip seal 72 which is secured in the outer race receiving bore of the impeller bearing mount cylinder 62. The upper end of shaft 68 is threaded at 73 and threadedly receives thereon the top 74 of the impeller which extends from the top down to the slinger flange 76 at the bottom and which is immediately above the bottom of the flask lower housing. The cylindrical wall 77 of the impeller has two additional circular flanges above the slinger flange 76. These are the blade support flange 78 and the blade hub cover flange 79. Two blades 81 are mounted in the annular groove 82 between the flanges 78 and 79 and pivotally secured in place by the pins 83 which are shoulder bolts screwed into the flange 78. The shape of these blades can be observed in FIG. 4 and FIG. 5. The blades are driven in the clockwise direction of arrow 86 in FIG. 4. Although the hub area of the blade is rectangular as shown in FIG. 5, the blade is tapered beginning at a line 87 (FIG. 4) to provide a sharp leading edge 88 while the trailing edge of the blade 89 is the full height of the hub portion. The blade is made of a tungsten carbide compound.

A "baffle" bar 91 is mounted on the inside upstanding cylindrical wall of the flask lower housing and extends up from near the bottom to a top edge 92. Thus, it presents a 90° angle edge 93 facing the materials as they are driven around by the impeller blades moving in the clockwise direction of arrow 86. Due to the inclination of the lower face of the blades downward from the front or leading edge toward the rear or trailing edge, as the blades rotate the trailing edge of each is closer to the bottom of the flask than is the sharp leading edge. This drives the waste materials downward and thus assures that they will be aggressively treated by the baffle during operation.

A removable flask cap 96 is provided in the central opening 97 at the top of the frustoconical surface of the flask top housing. This cap 96 has a tapered wall 98 so as to be manually insertable to the point of a snug fit, but can be readily removed manually, if desired, by means of the outwardly directed circular flange 99 at the top of the cap. The cabinet is provided with a lid 101 which is hinged to the upper rear wall 12R of the cabinet by adjustable hinges 102 such as the 500 Series marketed by Southco, Inc. of Concordville, Pa. 19331. These hinges are adjustable so that the lid can be raised at the front end edge in the direction of arrow 200 and can remain in virtually any position up to vertical. The underside of the lid has an inwardly projecting bulge 103 therein which, when the lid is closed, engages the flask cap 96 and assures that the cap will remain securely closed in place on the flask top housing. A bulb gasket may be provided around the perimeter of the cabinet lid to seal against the cabinet top during operation.

Referring to FIG. 6, a strainer cap 112 is shown. It is similar to cap 96, having a tapered wall 113 and perimetrical top flange 114 but, instead of a solid bottom, the bottom 116 is a screen. It may also have a handle tab 117 at the top flange.

Referring again to FIGS. 1 and 2, a control group 104 is provided on a boss 106 at the front of the cabinet and includes a momentary contact "ON" switch 107, an "EMERGENCY STOP" switch 108, and a pilot light 109 illuminated when the operating cycle is in progress. These are associated with suitable electrical circuitry to control the motor as desired. The circuitry is not shown herein as it may be conventional and well within the skill of the art.

Referring again to FIG. 4, a pair of T-type handles 111 may be provided on the side of the flask lower housing for a purpose which will be described now.

OPERATION

The flask assembly is removable from the main cabinet by simply lifting the cabinet lid and lifting the flask assembly out of the cabinet by use of the T-handles, one in each hand. The flask assembly can be easily lifted off the coupler and moved to whatever site location is convenient for deposit of medical waste material into it, wherever such material is being generated. Of course, if the unit is mounted on a moveable cart as in FIG. 1, the cart can be simply pushed to the site without removing the flask assembly from it. With the top cap 96 pulled out of the top of the flask assembly, the waste material can be simply dropped into the flask assembly through the top opening 97. The opening is large enough in diameter, four inches, for example, to readily receive syringes, bandage material, rubber gloves, culture plates and vials, for example. Such waste materials are preferably dropped directly into the opening as they are produced, rather than putting them in another container and then transferring them later to the flask. For example, as a bandage is removed from a subject, the bandage materials are placed directly into the flask. When the flask assembly has been filled to a level about even with the top of the flask lower housing or bowl 52, and if the flask assembly is separate from the main cabinet, it can then be returned to the main cabinet and placed on the cabinet tub bottom with the four feet 58 in the pockets 59. Simultaneously the impeller shaft socket is received on the coupler square 41. Then water is poured through the top opening 97, a pouch of decontaminant is added, and the top cap 96 is installed and the cabinet lid is closed. Then the start switch 107 is pushed. The lid may thereupon be locked by an automatic electrically operated lid latch (not shown). The motor is energized and drives the impeller. The blades are driven thereby in a circular path, clockwise as per arrow 86 in FIG. 4 around the impeller axis. As they do so, they begin to cut-up the waste material in the housing. Although the materials do provide some resistance to the blade action, the combined effects of the sharp leading edges 88 of the blades, and the centrifugal force, keep them deployed in a radially outward extending direction to continue to cut up the waste material. As this occurs, the slinger flange 76 at the bottom of the impeller assembly keeps the material moving outward and upward around the curved outer portion 55 of the flask lower housing wall 52. Thus, it is kept moving in a path outward and upward along the wall and then back down into the blades. Also, the presence of the vertical block (baffle) 91 provides an abutment which, to materials moving in the clockwise direction, is relatively sharp. In addition, it inhibits the free circular flow of material around the inner wall of the flask lower housing, tending to direct it back into the path of the blades. The baffle facilitates destruction of sharp items and facilitates cutting of soft materials. This processing continues as long as desired until it is either stopped by expiration of the "run" period of an automatic timer, or is manually stopped by pushing the emergency stop pad 108 to simply end the desired cycle. The pilot light serves as an indicator that a cycle is in process. This light may remain on for several minutes after the processing is complete in order to indicate to the operator that it is not yet time to open the lid, because the contents have not yet settled.

When the pilot light goes out, the operator can then open the lid, grip the T-handles, pull the flask assembly out of the tub of the main cabinet, and take it to a sink. The cap 96 is removed and replaced by the strainer 112 in the opening 97. Then the flask assembly is inverted in the sink, and the decontaminant solution, together with any other liquids which were contained in the waste material are drained into the sink. Then the flask assembly is righted and moved over to a solid waste receiver bucket or bag or the like, and the processed waste materials are dumped into the receiver for later disposal in a conventional waste container.

As a preferred alternative procedure, instead of using the strainer, the flask assembly can be dumped, liquids and solids simultaneously, into a disposable bag containing a liquid-absorbent gel compound. Then the flask is righted and ready for return the the waste generation site for collection of more waste in it.

With a machine built according to the present invention, in addition to the mincing action on materials, needles are bent and blunted as they are driven into the baffle. If it is ever desired to do so, the flask can be washed out without taking it apart, just as one could wash out a vase or bowl. If ever desired, such as for servicing interior components, the flask upper and lower housings can be separated by releasing the spring clamps 57. After servicing, they can be re-assembled, clamped together, and the flask assembly can be returned to the waste generation site for use again as described above.

As an example, the flask components can be made of spun stainless steel. Many of the more dense components, such as the impeller bearing mount cylinder, the impeller shaft, and the impeller itself, can be stainless steel investment castings. For a flask assembly that will hold and process approximately one gallon of medical waste materials in their final processed state, a drive motor of one horsepower is useful to complete a processing of that much material within a two minute cycle. An example of a suitable decontaminant solution is a one ounce package of A-33 dry decontaminant powder as marketed by Airkem Professional Products of St. Paul, Minn. Dumping of treated waste from the flask can be into a two gallon plastic bag of three mil membrane containing a polymeric absorbent powder which develops a gel as it absorbs the liquid. The bag preferably has a drawstring for convenient handling and can be placed in a conventional trash or garbage container. Although the description refers to a one-gallon version, it should be appreciated that the present invention can be applied to larger versions.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A method of treatment of medical waste material comprising the steps of:
   depositing the medical waste material in a closable collection and processing assembly at the site of generation of the medical waste material;
   processing the medical waste material collected in the collection and processing assembly by employing a power unit and driving a waste processor disposed within the processing assembly, said waste processor including moving blades and an adjacent abutment surface and edge to disintegrate the waste material deposited in the processing assembly; and
   dumping the processed medical waste material from the processing assembly into a waste receiver having an absorbent for liquid therein.

2. The method of claim 1 further comprising the step of:
   prior to dumping, placing a pouch of absorbent material in a plastic receiving bag to receive the dumped contents of the processing assembly.

3. The method of claim 1 further comprising the step of:

introducing a decontaminant material into the processing assembly prior to driving the waste processor.

4. The method of claim 1 further comprising the step of:
enclosing the processing assembly within the power unit during processing, and removing the processing assembly form the power unit after processing, and thereafter dumping the processed waste material for the processing assembly.

5. The method of claim 1 further comprising the step of:
moving the processing assembly to a processing site separate form the waste generation site; and thereafter
processing the waste material at the processing site.

6. The method of claim 1 wherein the step of employing the power unit is done by moving the processing assembly form the waste generation site to a separate power unit located at a remote processing site.

7. A method of treatment of medical waste material comprising the steps of:
providing a portable reusable medical waste collection, destruction and disinfection apparatus at a site of generation of the medical waste material, said portable reusable medical waste collection, destruction and disinfection apparatus including moveable blades and an adjacent abutment surface and cutting edge to mince and blunt and disinfect the medical waste material collected in said portable reusable medical waste collection, destruction and disinfection apparatus;
providing a separate power unit at a processing site separate form the waste generation site for driving said portable reusable medical waste collection, destruction and disinfection apparatus;
depositing the medical waste material in the portable reusable medical waste collection, destruction and disinfection apparatus at the site of generation of the waste material;
moving the portable reusable medical waste collection, destruction and disinfection apparatus and the medical waste while contained therein to the separate processing site;
placing the portable reusable medical waste collection, destruction and disinfection apparatus and the medical waste contained therein on the separate power unit located at the processing site; and
processing the waste material while contained in the portable reusable medical waste collection, destruction and disinfection apparatus at the processing site by operation of the power unit.

8. The method of claim 7 further comprising the step of:
introducing a decontaminant material into the portable reusable medical waste collection, destruction and disinfection apparatus prior to operating said power unit.

9. The method of claim 8 further comprising the step of:
removing the portable reusable medical waste collection, destruction and disinfection apparatus form the power unit after processing and disinfecting the waste material, and dumping the processed and disinfected waste material from the portable reusable medical waste collection, destruction and disinfection apparatus.

10. In a system for processing medical waste materials, a separate waste collection and processing assembly comprising:
means forming a chamber having a bottom, a generally upstanding side wall and an upper wall leading to a closable opening;
a central aperture in the bottom of the chamber;
an impeller support secured to the bottom of the chamber and projecting upward into the chamber around the central aperture and sealed around the central aperture to prevent discharge of the chamber contents through the central aperture;
a pair of spaced bearings mounted to the inner surface of the impeller support;
an impeller shaft mounted to said pair of bearings;
an impeller hub secured to the top of the impeller shaft and extending out, over and down around the impeller support to a lower edge near the bottom of the chamber, the impeller hub having an annular groove and blade support pins therein, and being rotatable in the chamber;
first and second blades pivotally mounted on the blade support pins, and projecting outwardly therefrom toward the upstanding side wall of the chamber; and
an abutment bar located on the side wall of the chamber providing an inwardly projecting and generally vertically extending abutment surface and edge located slightly outward of the blades in a position to be struck by waste material inside the chamber being driven against the abutment bar by the blades as they are rotated, the edge and abutment surface providing a cutting and blunting element in cooperation with said pivotably mounted blades.

11. The system of claim 10 wherein:
the blades have leading edges and trailing edges, the leading edges being sharpened; and
the blades have lower faces inclined downward from the leading edges to the trailing edges.

12. The system of claim 11 wherein:
the blades are made of a tungsten carbide compound.

13. The system of claim 10 wherein:
the impeller shaft, hub and bearings are coaxial on an axis;
said impeller hub forms a yoke including said annular groove for mounting said blades; and
the blades are pivotally mounted within said yoke on the pins and are free to be deployed radially outwardly form the pins by centrifugal force as the impeller hub is driven in rotation.

14. The system of claim 1 wherein said chamber-forming means comprises:
a separable upper wall secured to the side wall and having a generally conical surface extending upwardly and inwardly form the side wall to said central opening; and
a stop cap removably plugging the opening.

15. The system of claim 14 further comprising:
spring clips and over-center clamps holding the separable upper wall onto the side wall.

16. The system of claim 10 further comprising:
a cabinet unit carrying a drive motor and being adapted to couple said drive motor to said impeller shaft, and including a floor with upwardly opening sockets therein; and
wherein said chamber-forming means further comprises a plurality of feet extending downwardly form said chamber-forming means, said sockets being adapted to receive said feet to prevent rotation of said chamber-forming means as the impeller hub is rotated.

17. An apparatus for collecting and processing medical waste, comprising:
   a separate means forming a waste collection and processing chamber having a closable mouth, said chamber-forming means carrying an integral waste processing means within said chamber and being adapted at its exterior to mate with a separate power unit and to permit power to be transferred to and drive with integral waste processing means provided within the waste collection and processing chamber,
   said integral waste processing means comprising a plurality of hinged waste cutting and pulverizing element adapted to cooperate with an adjacent abutment surface and edge to comminute solid and non-solid medical waste; and
   a power unit adapted to mate with said separate chamber-forming means and to couple with and transfer power to said integral waste processing means provided within said separate chamber-forming means to comminute the medical waste collected within the waste collection and processing chamber.

18. The system of claim 17 wherein said integral waste processing means comprises a rotatable hub carrying said plurality of hinged waste cutting and pulverizing elements,
   said chamber-forming means comprises a bearing assembly for carrying said rotatable hub and includes at least one exterior surface portion adapted to engage said power unit, and
   said power unit includes a motor having a drive shaft to engage and drive the rotatable hub of said integral waste processing means, and at least one surface portion adapted to engage said at least one exterior surface potion of said chamber-forming means to prevent rotation of said chamber-forming means.

19. The apparatus of claim 18 wherein said bearing assembly of said chamber-forming means comprises a cylinder extending upwardly within the central portion of said waste collection and processing chamber and carrying, within the chamber, bearing means for said hub, said hub including an exterior cylindrical portion extending downward outside said cylinder and carrying thereon said plurality of hinged waste cutting and pulverizing elements and further including an interior shaft portion carried by said bearing means and adapted to its end for engagement by the drive shaft of the motor of said power unit.

20. The apparatus of claim 19 wherein said bearing assembly cylinder extends upwardly within the waste collection and processing chamber a distance sufficient to form a dam shielding said baring means from liquid within said waste collection and processing chamber and to carrying spaced upper and lower bearings between said bearing assembly cylinder and said interior shaft portion of said rotatable hub.

21. The apparatus of claim 20 further comprising a spacer between said upper bearing and said rotatable hub to maintain the location of said rotatable hub on said baring assembly.

22. The apparatus of claim 19 further comprising a liquid seal between said bearing assembly cylinder and said rotatable hub.

23. The apparatus of claim 18 wherein said plurality of hinged waste cutting and pulverizing elements comprise blade-like members having thin leading edges and lower faces inclined at an acute angle with respect to the bottom of the waste collection and processing chamber.

24. The apparatus of claim 23 wherein said chamber-forming means has a cylindrical interior side surface portion extending around said blade-like members and an upper interior surface portion extending from said cylindrical side portion over said blade-like members to redirect waste material urged upwardly along the cylindrical side wall by said blade-like members back to the central portion of said waste collecting and processing chamber.

25. The apparatus of claim 24 wherein said upper interior surface of said waste collecting and processing chamber is generally frustoconical and forms said closable mouth.

* * * * *

UNITED STATES PATENT AND TRADEMARK OFFICE
CERTIFICATE OF CORRECTION

PATENT NO. : 5,240,187

Page 1 of 2

DATED : August 31, 1993

INVENTOR(S) : Joseph H. Wilson

It is certified that error appears in the above-identified patent and that said Letters Patent is hereby corrected as shown below:

On the Cover Page, line 13 of the Abstract paragraph, change "absorber" to --absorbent--.

In Col. 1, line 12, change "ha" to --has--.

In Col. 4, line 14, after the word "rotate" add --,-- (comma)

In Col. 6, line 2, change first occuring "the" to --to--.

In Col. 7, line 8, change "form" to --from--.

In Col. 7, line 10, change "for" to --from--.

In Col. 7, line 11, change "step" to --steps--.

In Col. 7, line 14, change "form" to --from--.

In Col. 7, line 19, change "form" to --from--.

In Col. 7, line 34, change "form" to --from--.

In Col. 7, line 63, change "form" to --from--.

In Col. 8, line 49, change "form" to --from--.

In Col. 8, line 55, change "form" to --from--.

In Col. 8, line 57, change "stop" to --top--.

In Col. 8, line 68, change "form" to --from--.

In Col. 9, line 17, change "element" to --elements--.

UNITED STATES PATENT AND TRADEMARK OFFICE
CERTIFICATE OF CORRECTION

PATENT NO. : 5,240,187

DATED : August 31, 1993

INVENTOR(S) : Joseph H. Wilson

It is certified that error appears in the above-identified patent and that said Letters Patent is hereby corrected as shown below:

In Col. 9, line 27, change "system" to --apparatus--.

In Col. 10, line 7, change "to" to --at--.

In Col. 10, line 13, change "baring" to --bearing--.

In Col. 10, line 15, change "carrying" to --carry--.

In Col. 10, line 21, change "baring" to --bearing--.

Signed and Sealed this

First Day of November, 1994

Attest:

BRUCE LEHMAN

Attesting Officer

Commissioner of Patents and Trademarks